(12) United States Patent
Hannigan et al.

(10) Patent No.: US 7,144,390 B1
(45) Date of Patent: Dec. 5, 2006

(54) NEGATIVE PRESSURE TREATMENT SYSTEM WITH HEATING AND COOLING PROVISION

(75) Inventors: Raymond R. Hannigan, San Antonio, TX (US); James R. Leininger, San Antonio, TX (US); Charles I. Biltz, Jr., San Antonio, CA (US); Frank Dilazzaro, San Antonio, CA (US); Christopher Fashek, San Antonio, CA (US); Wayne J. Schroeder, San Antonio, CA (US); Royce W. Johnson, Universal City, TX (US)

(73) Assignee: Kinetic Concepts, Inc., San Antonio, TX (US)

( * ) Notice: Subject to any disclaimer, the term of this patent is extended or adjusted under 35 U.S.C. 154(b) by 0 days.

(21) Appl. No.: 09/937,937

(22) PCT Filed: Mar. 31, 2000

(86) PCT No.: PCT/US00/08759

§ 371 (c)(1),
(2), (4) Date: Oct. 2, 2001

(87) PCT Pub. No.: WO00/59418

PCT Pub. Date: Oct. 12, 2000

Related U.S. Application Data

(60) Provisional application No. 60/127,596, filed on Apr. 2, 1999.

(51) Int. Cl.
*A61M 1/00* (2006.01)
*A61M 35/00* (2006.01)

(52) U.S. Cl. ............ 604/313; 604/304; 604/305; 604/290; 604/291

(58) Field of Classification Search ............ 604/289, 604/294, 291, 304–308, 290, 313–316; 602/41–43, 602/46, 48; 128/888, 889
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,367,332 A | 2/1968 | Groves |
| 3,520,300 A | 7/1970 | Flower |
| 3,648,692 A | 3/1972 | Wheeler |

(Continued)

FOREIGN PATENT DOCUMENTS

AU 550575 A1 8/1982

(Continued)

OTHER PUBLICATIONS

International Search Report for PCT international application PCT/GB95/01983; Nov. 23, 1995.

(Continued)

*Primary Examiner*—Kim M. Lewis

(57) ABSTRACT

A method, and apparatus (10) for the controlled acceleration, and/or retardation of the body's inflammatory response generally comprises a foam pad (11) for insertion substantially into a wound site, a heating, a cooling pad (13) for application over the wound site (12), a wound drape (14) or sealing enclosure of the foam pad (11), the heating, and cooling pad (13) at wound site (12). The foam pad (11) is placed in fluid communication with a vacuum source for promotion of the controlled acceleration or retardation of the body's inflammatory response. The heating, and cooling provision controls the local metabolic function as part of the inflammatory response.

12 Claims, 1 Drawing Sheet

U.S. PATENT DOCUMENTS

| | | | |
|---|---|---|---|
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez | |
| 4,165,748 A | 8/1979 | Johnson | |
| 4,233,969 A | 11/1980 | Lock et al. | |
| 4,245,630 A | 1/1981 | Lloyd et al. | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A * | 5/1983 | Svedman | 604/291 |
| 4,392,853 A | 7/1983 | Muto | |
| 4,392,858 A | 7/1983 | George et al. | |
| 4,419,097 A | 12/1983 | Rowland | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vailancourt | |
| 4,540,412 A | 9/1985 | Van Overloop | |
| 4,543,100 A | 9/1985 | Brodsky | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,949 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,086,771 A | 2/1992 | Molloy | |
| 5,092,858 A | 3/1992 | Benson et al. | |
| 5,100,396 A | 3/1992 | Zamierowski | |
| 5,134,994 A | 8/1992 | Say | |
| 5,149,331 A * | 9/1992 | Ferdman et al. | 604/290 |
| 5,167,613 A | 12/1992 | Karami et al. | |
| 5,176,663 A | 1/1993 | Svedman et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,344,415 A | 9/1994 | Debusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,345,623 B1 | 2/2002 | Heaton et al. | |
| 6,398,767 B1 * | 6/2002 | Fleischmann | 604/313 |
| 6,488,643 B1 | 12/2002 | Tumey et al. | |
| 6,493,568 B1 | 12/2002 | Bell et al. | |
| 6,553,998 B1 | 4/2003 | Heaton et al. | |
| 6,814,079 B1 | 11/2004 | Heaton et al. | |
| 2002/0115951 A1 | 8/2002 | Norstream et al. | |
| 2002/0120185 A1 | 8/2002 | Johnson | |
| 2002/0143286 A1 | 10/2002 | Tumey | |

FOREIGN PATENT DOCUMENTS

| | | |
|---|---|---|
| AU | 745271 | 3/2002 |
| AU | 755496 | 12/2002 |
| CA | 2005436 | 6/1990 |
| DE | 26 40 413 A1 | 3/1978 |
| DE | 43 06 478 A1 | 9/1994 |
| DE | 295 04 378 U1 | 9/1995 |
| EP | 0117632 A2 | 1/1984 |
| EP | 0100148 | 2/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 197 789 A | 6/1988 |
| GB | 2333965 A | 8/1999 |
| GB | 2329127 B | 8/2000 |
| SG | 71559 | 4/2002 |
| WO | WO 80/02182 | 10/1980 |
| WO | WO 93/09727 | 5/1993 |
| WO | WO/94/20041 | 9/1994 |
| WO | WO 96/05873 | 2/1996 |
| WO | WO 97/18007 | 5/1997 |
| WO | WO98/23236 | 6/1998 |
| WO | PCT/GB98/02713 | 9/1998 |

OTHER PUBLICATIONS

Patent Abstract of Japan; JP4129536; Terumo Corporation; Apr. 30, 1992.

PCT International Search Report; PCT international application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB96/02802; Sep. 3, 1997.

Louis C. Argenta, MD and Michael J. Morykwas, PHD; Vacuum-Assisted Closure: A New Method for Wound Control and Treatment: Clinical Experience; Annals of Plastic Surgery, vol. 38, No. 6, Jun. 1997, pp. 563-577; Lippincott Williams & Wilkins, Inc., Philadelphia, PA, U.S.A.

Susan Mendez-Eastman, RN; When Wounds Won't Heal, RN Jan. 1998, vol. 61(1); Medical Economics Company, Inc., Montvale, NJ, USA.

James H. Blackburn II, MD et al.; Negative-Pressure Dressings as a Bolster for Skin Grafts; Annals of Plastic Surgery, vol. 40, No. 5, May 1998, pp. 453-457; Lippincott Williams & Wilkins, Inc., Philadelphia, PA, USA.

John Masters; Letter to the editor; British Journal of Plastic Surgery, 1998, vol. 51(3), p. 267: Elsevier Science/The British Association of Plastic Surgeons, United Kingdom.

S.E. Greer, et al.; The Use of Subatmospheric Pressure Dressing Therapy to Clos Lymphocutaneous Fistulas of the Groin; British Journal of Plastic Surgery (2000), 53, p. 484-487, Article No. BJPS2000.3360, Elsevier Science/The British Association of Plastic Surgeons, United Kingdom.

George V. Letsou, M.D., et al. .; Stimulation of Adenylate Cyclase Activity in Cultured Endothelial Cells Subjectied to Cyclic Stretch; Journal of Cardiovascular Surgery, 31, 1990, pp. 634-639; Edizonia Minerva Medica, Torino, Italy.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts For the Clinical-Biological Management of the Wound Process in the Treatment of Purulent Wounds by Means of Vacuum Therapy; Vestnik Khirurgi.

* cited by examiner

NEGATIVE PRESSURE TREATMENT SYSTEM WITH HEATING AND COOLING PROVISION

RELATED APPLICATION

This application claims priority to United States provisional patent application Ser. No. 60/127,596 entitled VACUUM ASSISTED CLOSURE SYSTEM WITH HEATING AND COOLING PROVISION filed Apr. 2, 1999. By this reference, the full disclosure, including the drawings, of U.S. provisional patent application Ser. No. 60/127,596 is incorporated herein.

TECHNICAL FIELD

The present invention relates to the healing of wounds. More specifically, the present invention relates to the vacuum assisted closure of wounds wherein localized heating or cooling is used to accelerate or retard the metabolic function of the inflammatory system in order to facilitate wound healing.

BACKGROUND ART

Wound closure involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion, whereafter cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but are also less able to successfully fight bacterial infection and thus are less able to naturally close the wound. Until recently, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples causes very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative pressure, commonly referred to as vacuum assisted closure (VAC) therapy, typically involves mechanical-like contraction of the wound with simultaneous removal of excess fluid. In this manner, VAC therapy augments the body's natural inflammatory process while alleviating many of the known intrinsic side effects, such as the production of edema caused by increased blood flow absent the necessary vascular structure for proper venous return.

While VAC therapy has been highly successful in the promotion of wound closure, healing many wounds previously thought largely untreatable, some difficulty remains. Because the inflammatory process is very unique to the individual patient, even the addition of VAC therapy does not result in a fast enough response for closure of some wounds, especially when applied during the occlusion and initial cleanup and rebuilding stages. It is therefore a principle object of the present invention to provide a method and apparatus whereby the known VAC therapy modalities are improved through controlled acceleration of the inflammatory response.

Additionally, and again at least partially attributable to the variance between patients, it is possible that a properly initiated inflammatory response may be taken too far, resulting in edema and pain. It is therefore another principle object of the present invention to provide a method and apparatus whereby the known VAC therapy modalities are improved through controlled retardation of the inflammatory response.

DISCLOSURE OF THE INVENTION

In accordance with the foregoing objects, the present invention—a method and apparatus for the controlled acceleration and/or retardation of the body's inflammatory response—generally comprises a foam pad for insertion substantially into a wound site, a heating and cooling pad for application over the wound site and a wound drape for sealing enclosure of the foam pad and the heating and cooling pad at the wound site. According to the invention, the foam pad is placed in fluid communication with a vacuum source for promotion of fluid drainage while warm or cool fluid is circulated through the heating and cooling pad for the controlled acceleration or retardation, respectively, of the metabolic function portion of the body's inflammatory response.

According to the preferred embodiment of the present invention, a heating and cooling provision is added to the previously known VAC therapy to control the local metabolic function as part of the inflammatory response. By providing localized heating in combination with the otherwise ordinary VAC therapy, the overall inflammatory response can be synergistically accelerated to produce rapid capillary occlusion and earlier initiation of the cleanup and rebuilding stages. Likewise, in the event that the attending clinician determines that the inflammatory response has been over-activated, localized cooling may be provided in combination with the VAC therapy to retard the body's inflammatory response without sacrifice of the edema control and other aspects of the otherwise provided VAC therapy.

In the preferred embodiment of the present invention, the heating and cooling pad comprises a flexible and breathable water layer, generally comprising two sheets of RF-weldable material. The two sheets of the pad are RF-welded together in a waffle-like pattern, wherein a plurality of apertures is formed between a plurality of channels. The apertures allow the transpiration of moisture from the patient's skin while the channels allow the circulation, via a supply tube and a drainage tube, of warm or cool water, as required, through the pad for the heating or cooling thereof.

While the heating and cooling pad may be placed inside or outside of the wound drape during the heating aspect of the present invention, it is critical that the heating and cooling pad be placed inside of the wound drape during the cooling aspect of the present invention. In this manner, condensate formation on the interior of the drape, which may cause the drape's adhesive to loosen and ultimately result in loss of vacuum at the wound site, can be minimized. In particular, placing the heating and cooling pad inside the wound drape limits the surrounding moisture content to that existing and generated within the confines of the wound site, which is minimized by the suction aspect of the VAC therapy.

Because the cooling aspect of the present invention should be implemented in this manner and the clinician may indicate the need for cooling at any time after initiation of VAC therapy, the preferred method of the present invention comprises placing the heating and cooling pad beneath the wound drape, adjacent the foam pad and wound site, regardless of whether heating or cooling is initially indicated. Upon placement of the pad, the wound drape is firmly adhered about the supply tube and drainage tube to prevent vacuum leakage.

Finally, many other features, objects and advantages of the present invention will be apparent to those of ordinary skill in the relevant arts, especially in light of the foregoing discussions, the following drawings and exemplary detailed description and the claims appended hereto.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

BEST MODE FOR CARRYING OUT THE INVENTION

Figure 1:
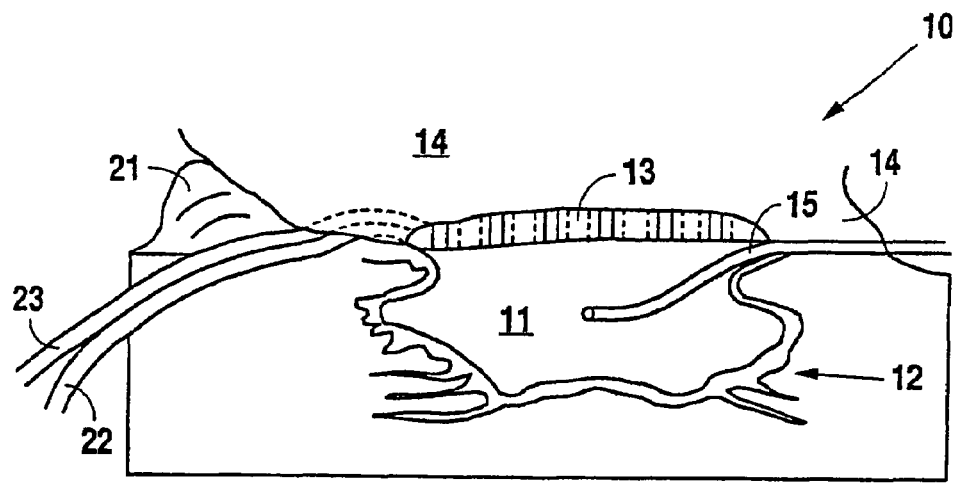
FIG. 1 shows, in partially cut away perspective view, the preferred embodiment of the present invention as applied to a mammalian wound site.
Figure 2:
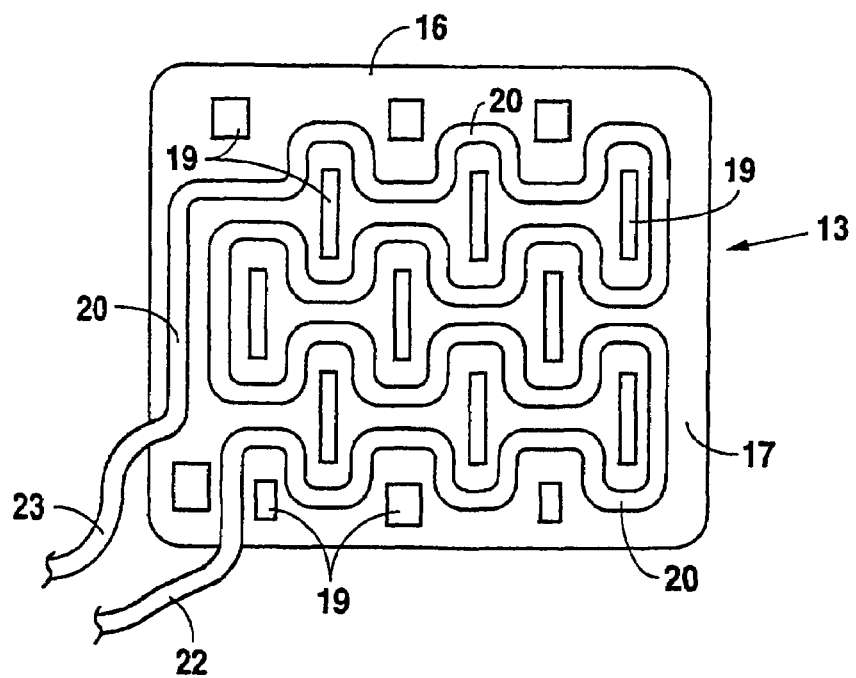
FIG. 2 shows, in top cross-sectional plan view, the heating and cooling pad of the invention of FIG. 1.

Although those of ordinary skill in the art will readily recognize many alternative embodiments, especially in light of the illustrations provided herein, this detailed description is exemplary of the preferred embodiment of the present invention—a vacuum assisted closure system with heating and cooling provision, the scope of which is limited only by the claims appended hereto.

Referring now to the figures, the present invention 10 is shown to generally comprise a foam pad 11 for insertion substantially into a wound site 12, a heating and cooling pad 13 for application over the wound site 12 and a wound drape 14 for sealing enclosure of the foam pad 11 and the heating and cooling pad 13 at the wound site 12. According to the invention, the foam pad 11 is placed in fluid communication with a vacuum source for promotion of fluid drainage while warm or cool fluid is circulated through the heating and cooling pad 13 for the controlled acceleration or retardation, respectively, of the metabolic function portion of the body's inflammatory response.

According to the preferred embodiment of the present invention, the foam pad 11, wound drape 14 and vacuum source are implemented as known in the prior art, each of which is detailed in U.S. patent application Ser. No. 08/517,901 filed Aug. 22, 1995. By this reference, the full disclosure of U.S. patent application Ser. No. 08/517,901 ("the '901 application"), including the claims and the drawings, is incorporated herein as though now set forth in its entirety. Additionally, such a VAC system is readily commercially available through Kinetic Concepts, Inc. of San Antonio, Tex., U.S.A. and/or its subsidiary companies.

As detailed in the '901 application, the foam pad 11 preferably comprises a highly reticulated, open-cell polyurethane or polyether foam for good permeability of wound fluids while under suction. As also detailed in the '901 application, the foam pad 11 is preferably placed in fluid communication, via a plastic or like material hose 15, with a vacuum source, which preferably comprises a canister safely placed under vacuum through fluid communication, via an interposed hydrophobic membrane filter, with a vacuum pump. Finally, the '901 application also details the wound drape 14, which preferably comprises an elastomeric material at least peripherally covered with a pressure sensitive, acrylic adhesive for sealing application over the wound site 12.

According to the preferred method of the present invention, those components as are described in the '901 application are generally employed as known in the art with the exception that the heating and cooling provision of the present invention is added to control the local metabolic function as part of the inflammatory response. By providing localized heating in combination with the otherwise ordinary VAC therapy, the overall inflammatory response can be synergistically accelerated to produce rapid capillary occlusion and earlier initiation of the cleanup and rebuilding stages. Likewise, in the event that the attending clinician determines that the inflammatory response has been overactivated, localized cooling may be provided in combination with the VAC therapy to retard the body's inflammatory response without sacrifice of the edema control and other aspects of the otherwise provided VAC therapy.

In the preferred embodiment of the present invention, the heating and cooling pad 13 comprises a flexible and breathable water layer 16, generally comprising two sheets 17 (one not shown) of RF-weldable material. The two sheets 17 of the pad are RF-welded together in a waffle-like pattern, wherein a plurality of apertures 19 is formed between a plurality of channels 20. The apertures 19 allow the transpiration of moisture from the patient's skin 21 while the channels 20 allow the circulation, via a supply tube 22 and a drainage tube 23, of warm or cool water, as required, through the pad 13 for the heating or cooling thereof.

While the heating and cooling pad 13 may be placed inside or outside of the wound drape 14 during the heating aspect of the present invention, it is critical that the heating and cooling pad 13 be placed inside of the wound drape 14 during the cooling aspect of the present invention. In this manner, condensate formation on the interior and near the edges of the drape 14, which may cause the drape's adhesive to loosen and ultimately result in loss of vacuum at the wound site 12, can be minimized. In particular, placing the heating and cooling pad 13 inside the wound drape 14 limits the surrounding moisture content to that moisture level existing and generated within the confines of the wound site 12, which is minimized by the suction aspect of the VAC therapy.

Because the cooling aspect of the present invention should be implemented in this manner and the clinician may indicate the need for cooling at any time after initiation of VAC therapy, the preferred method of the present invention comprises placing the heating and cooling pad 13 beneath the wound drape 14, adjacent the foam pad 11 and wound site 12, regardless of whether heating or cooling is initially indicated. Upon placement of the pad 13, the wound drape 14 is firmly adhered about the supply tube 22 and the drainage tube 23 to prevent vacuum leakage.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and the claims drawn hereto. For example, those of ordinary skill in the art will recognize that the heating and cooling pad 13 may be constructed in a wide variety of shapes, sizes and internal structures. Such an alternative embodiment may comprise the integration of the heating and cooling pad 13 into a multi-layered version of the wound drape 14. In any case, because the scope of the present invention is much broader than any particular embodiment, the foregoing detailed description should not be construed as a limitation of the present invention, which is limited only by the claims appended hereto.

INDUSTRIAL APPLICABILITY

The present invention is applicable to the wound healing arts.

What is claimed is:

1. A device for promoting wound healing in mammals, comprising:
    a negative pressure source;
    a pad for placement within a wound of a mammal;
    a drape for sealing and enclosing said pad on said wound and for maintaining a reduced pressure within said wound;
    a fluid communication means for communicating between said negative pressure source and said pad; and
    a heating element for actively heating said pad;
    wherein said heating element is in contact with said pad;
    wherein said heating element comprises at least two sheets having a plurality of apertures and fixedly connected such that said apertures form a plurality of fluid channels.

2. A device for promoting wound healing in mammals, comprising:
    a negative pressure source;
    a pad for placement within a wound of a mammal;
    a drape for sealing and enclosing said pad on said wound and for maintaining a reduced pressure within said wound;
    a fluid communication means for communicating between said negative pressure source and said pad;
    a heating element for actively heating said pad; and
    a cooling element for actively cooling said pad subsequent to heating said pad; and wherein said cooling element comprises at least two sheets having a plurality of apertures and fixedly connected such that said apertures form a plurality of fluid channels.

3. The device according to claim 2 further comprising a source of warm fluid for circulation through said fluid channels.

4. The device according to claim 2 further comprising a source of cool fluid for circulation through said fluid channels.

5. A device for promoting wound healing in mammals, comprising:
    a negative pressure source;
    a pad for placement within a wound of a mammal;
    a cover for maintaining a reduced pressure within the wound;
    a fluid communication means for communication between said negative pressure source and said pad; and
    a cooling element for actively cooling said pad, wherein said cover is interposed between said pad and said cooling element.

6. The device according to claim 5 wherein said cooling element comprises at least two sheets having a plurality of apertures and fixedly connected such that said apertures form a plurality of fluid channels.

7. The device according to claim 6 further comprising a source of cool fluid for circulation through said fluid channels.

8. The device according to claim 5 further comprising a heating element for actively heating said pad subsequent to cooling said pad, and wherein said heating element comprises at least two sheets having a plurality of apertures and fixedly connected such that said apertures form a plurality of fluid channels.

9. The device according to claim 8 further comprising a source of warm fluid for circulation through said fluid channels.

10. A device for promoting wound healing in mammals, comprising:
    a negative pressure source;
    a pad for placement within a wound of a mammal;
    a cover for maintaining a reduced pressure within said wound;
    a fluid communication means for communicating between said negative pressure source and said pad; and
    a heating and cooling pad for affecting metabolic function at said wound, and positioned proximate said pad.

11. The device according to claim 10 wherein said heating and cooling pad comprises at least two sheets having a plurality of apertures and fixedly connected such that said apertures form a plurality of fluid channels.

12. The device according to claim 10 further comprising a source of warm or cool fluid for circulation through said fluid channels.

* * * * *